United States Patent [19]

Ruf

[11] Patent Number: 5,068,374

[45] Date of Patent: Nov. 26, 1991

[54] METHOD FOR THE PREPARATION OF ANHYDROUS TIN-DICARBOXYLATE-DIHALIDES

[75] Inventor: Erich Ruf, Essen-Haarzopf, Fed. Rep. of Germany

[73] Assignee: T. Goldschmidt AG, Essen, Fed. Rep. of Germany

[21] Appl. No.: 647,402

[22] Filed: Jan. 29, 1991

[30] Foreign Application Priority Data

Feb. 17, 1990 [DE] Fed. Rep. of Germany ....... 4005135

[51] Int. Cl.$^5$ ................................................ C07F 7/22
[52] U.S. Cl. ................................................ 556/105
[58] Field of Search ........................................ 556/105

[56] References Cited

U.S. PATENT DOCUMENTS 4,495,105  1/1985  Miller ................................... 260/414
4,795,820  1/1989  Synoradzki et al. ................. 556/105

FOREIGN PATENT DOCUMENTS 1174435  8/1985  U.S.S.R. .............................. 556/105

Primary Examiner—José G. Dees
Assistant Examiner—Porfirio Nazario
Attorney, Agent, or Firm—Toren, McGeady & Associates

[57] ABSTRACT

A method is disclosed for the preparation of anhydrous tin-dicarboxylate-dihalide. Anydrous tin-(II)-halide is reacted with an excess amount of acetic acid anhydride at temperatures of about between 20° to 100° C. while passing oxygen through the reaction mixture or adding an oxygen yielding agent such as hydrogen peroxide. The tin-diacetate-dihalide thus formed is separated and is further reacted with aliphatic carboxylic acid having more than 4 carbon atoms or the corresponding acid anhydrides at the temperatures of 80° to 150° C. while the liberated acetic acid anhydride or acetic acid is removed by distillation.

7 Claims, No Drawings

METHOD FOR THE PREPARATION OF ANHYDROUS TIN-DICARBOXYLATE-DIHALIDES

FIELD OF INVENTION

The invention generally relates to organic tin compounds and is particularly directed to a method for the preparation of anhydrous tin-dicarboxylate-dihalides.

BACKGROUND INFORMATION AND PRIOR ART

The reaction of tin-(IV)-chloride with acetic acid has previously been described in the literature. See Gmelin, 8th Ed., 1975, No. 46, part C 2, p. 221. In this prior art reaction, the reaction mixture is heated to 80° C. and is carefully concentrated at this temperature under vacuum conditions whereby tin-diacetate-dichloride is formed. However, this method results in the formation of the tin-diacetate-dichloride in very small yields only and thus is unsuitable for industrial production in an economic manner. Furthermore, the procedure referred to is hazardous from an environmental and health point of view, since tin-(IV)-chloride is a fuming liquid which readily hydrolizes.

The literature is devoid of references in respect of the production of other tin-dicarboxylate-dihalides such as, for example, tin-diacetate-difluoride, tin-diacetate-dibromide or tin-diacetate-diiodide. The same applies to tin-dicarboxylate-dihalides with high molecular carboxylate groups.

OBJECTS OF THE INVENTION

It is the primary object of the invention to provide a method for the production of anhydrous tin-dicarboxylate-dihalides which is simple to carry out, economical and results in high yields.

Generally it is an object of the invention to improve on the art of producing anhydrous organic tin compounds.

SUMMARY OF THE INVENTION

Pursuant to the invention, anhydrous tin-dicarboxylate-dihalides are produced in a two-stage process. In the first stage, tin-diacetate-dihalides are produced which, in the second stage, are reacyloxylated into the desired tin-dicarboxylate-dihalides with the corresponding carboxylic acids or acid anhydrides.

Thus, briefly, in the first stages anhydrous tin-(II)-halide is reacted with an excess of acetic acid anhydride at temperatures of about between 20° to 100° C. while passing oxygen through the reaction mixture or adding an oxygen yielding agent to the reaction mixture to form tin-diacetate-dihalide. The halide is separated from the reaction mixture and, in the second stage, is reacted with aliphatic carboxylic acid with more than four carbon atoms or with the corresponding acid anhydride. This reaction is carried out at temperature of between about 80° to 150° C. and the liberated acetic acid anhydride or acetic acid is removed by vacuum distillation.

In a preferred embodiment of the invention, the second stage is carried out with saturated or unsaturated aliphatic carboxylic acids with up to 22 carbon atoms or their corresponding acid anhydrides.

1. First Method Stage

It is advantageous if the first method stage is carried out in the presence of acetic acid as solvent. In this manner, the tin-diacetate-dihalides which are formed remain in solution for a longer period of time which, in turn, results in a more rapid reaction.

As to the oxygen yielding agent, an aqueous hydrogen peroxide solution is advantageously used. In order to obtain the desired water-free tin-diacetate-dihalides, it is then necessary to transfer the water, which has been introduced into the reaction mixture by way of the hydrogen peroxide solution, into acetic acid by adding corresponding amounts of acetic acid anhydride. The reaction period is usually 2 to 7 hours, whereupon the reaction mixture is cooled. During the reaction and because of its exothermic nature, the reaction mixture becomes rather hot and thus may be cooled to avoid excess temperatures. Tin-precipitating diacetate-dihalides are removed by filtration and dried. The yield of white anhydrous tin-diacetate-dihalide is between about 70 to 90%.

In a preferred embodiment of the invention, the reaction of the anhydrous tin-(II)-dihalides with an excess amount of acetic acid anhydride is carried out at temperatures of about between 30° to 90° C. In view of the fact that the reaction of the tin-dihalide in acetic acid anhydride while passing oxygen through the mixture is strongly exothermic, it is advantageous to maintain the reaction mixture within the indicated temperature range by cooling. In this manner, yields of about 90 to 100% are obtained.

As to the tin-(II)-halides, the chloride, bromide, iodide and also the fluoride may be used. Advantageously, in view of its greatest accessiblity, tin-(II)-chloride is used.

The first stage of the inventive method has the advantage that starting products are used which are relatively inexpensive and which are easily handled without any environmental or health risks, and that the desired tin-diacetate-dihalide is obtained in high yields.

2. Second Method Stage

In the second stage of the inventive procedure, the anhydrous tin-diacetate-dihalides obtained in the first stage are reacted with aliphatic carboxylic acids with more than four carbon atoms or their corresponding acid anhydrides. The reaction is carried out at temperatures of about between 80° to 150° C. while at the same time distilling off the liberated acetic acid anhydride or acetic acid under reduced pressure. In this manner, the corresponding tin-dicarboxylate-dihalides are obtained in a simple way in anhydrous form. In a preferred embodiment, the reaction of tin-diacetate-dihalides with the aliphatic carboxylic acids with more than four carbon atoms or their acid anhydrides is carried out at temperatures of 100° to 110° C. under slight vacuum conditions. The tin-dicarboxylate-dihalides of the carboxylic acids or acid anhydrides used are then obtained in substantially quantitative yield.

Examples of suitable carboxylic acids with more than four carbon atoms suitable for the inventive purposes are:

(a) saturated aliphatic carboxylic acids such as valeric acid, caprylic acid, undecanoic acid, myristic acid, palmitic acid, stearic acid and behane acid;

(b) unsaturated aliphatic carboxylic acids such as oleic acid and linoleic acid.

Examples of suitable acid anhydrides are propionic acid anhydride, butyric acid anhydride, valeric acid anhydride, lauric acid anhydride and stearic acid anhydride.

The anhydrous tin-diacetate-dihalides obtained in the first stage of the procedure may serve as tin-base compounds in the application of electrically conductive and infrared reflecting layers on glass or ceramic surfaces. Further, tin-diacetate-dihalides, per se, or in suitable formulations can be used for the chemical preservation of glass surfaces. A further field of use for tin-diacetate-dihalides is the production of tin-containing metal oxane compounds.

The invention will now be described by a number of examples, it being understood that these examples are given by way of illustration and not by way of limitation. Examples 1 through 5 are directed to the preparation of the anhydrous tin-diacetate-dihalides (first stage of the inventive method) while examples 6 through 11 are concerned with the preparation of the tin-dicarboxylate-dihalides (second stage of the inventive procedure).

EXAMPLE 1

This experiment was carried out in a 1 liter reaction vessel of the plane ground type having a sintered glass frit bottom and being fitted with a thermometer, cooler and mixer. 538.5 gram of acetic acid anhydride are charged into the reaction vessel. While activating the mixer, 189.6 gram of tin-(II)-chloride are added. A slurry is obtained through which oxygen is passed with strong agitation.

In view of the exothermic nature of the reaction, the reaction mixture heats up considerably. By means of a cooling bath, the reaction mixture is, however, maintained in a temperature range of 30° to 50° C. Instead of a cooling bath, the cooling can be accomplished by discontinuous introduction of an inert gas, for example, argon or nitrogen.

The tin-diacetate-dichloride formed during the procedure precipitates directly. The reaction time amounts to about 6 hours. The tin-diacetate-dihalide formed in this manner is removed by filtration and is dried under vacuum conditions (about 2 mm Hg). The yield was 277.6 gram of tin-diacetate-dichloride.

EXAMPLE 2

This experiment was carried out in the same type of reaction vessel as referred to in Example 1. 204.0 gram of acetic acid anhydride and 420 gram of acetic acid are introduced into the vessel. Under agitation, 189.6 gram of water-free tin-(II)-chloride are added to the mixture. While strongly agitating, oxygen is passed through the mixture. The reaction mixture is maintained at a temperature range of about 30° to 50° C. by cooling. The reaction period is about 2 hours.

A fine white suspension is obtained which is transferred into a 1 liter single neck flask and is subsequently concentrated in a rotation evaporator at about 80° C. in a water jet vacuum to obtain a dry product.

The yield was 307.7 gram of tin-diacetate-dichloride.

EXAMPLE 3

This experiment was carried out in a 2 liter reaction vessel of the plane ground type fitted with a thermometer, cooler, drop funnel and stirrer. 1,260 gram of acetic acid anhydride are introduced into the reaction vessel. 758.4 gram of anhydrous tin-(II)-chloride are added under stirring. A slurry is obtained in this manner.

While stirring strongly, 194.3 gram of hydrogen peroxide solution (70%) are slowly added to the slurry in drop-wise manner. In view of the pronounced exothermic reaction, the reaction mixture is cooled to maintain it in a temperature range of about 30° to 40° C. The reaction period was about 7 hours.

The tin-diacetate-dichloride obtained in this manner precipitates immediately and is removed by filtration through a sintered glass disc and is washed four times with 100 ml chloroform each. Subsequently the product is dried under vacuum (about 2 mm Hg).

The yield was 1,104.8 gram of tin-diacetate-dichloride.

EXAMPLE 4

This experiment was carried out in a 250 ml four neck flask fitted with a thermometer, cooler, stirrer and drop funnel. 110.2 gram of acetic acid anhydride are added to the flask. 37.2 gram of tin-(II)-iodide are added under stirring to the flask. Thereafter, while strongly agitating, 11.4 gram of hydrogen peroxide solution (30%) are added in drop-wise manner. Since the reaction is strongly exothermic, the flask was placed into a cooling bath to maintain the reaction mixture at a temperature range of about 30° to 40° C. The reaction period was about 2 hours.

The tin-diacetate-diiodide suspension obtained in this manner was cooled to −10° C. Tin-diacetate-diiodide was removed by filtration and was washed five times with about 100 ml of hexane each. Subsequently the product was dried in vacuum (about 2 mm Hg).

The yield was 36.2 gram of tin-diacetate-diiodide.

EXAMPLE 5

This experiment was carried out in a 1 liter polyethylene flask fitted with a gas inlet tube, cooler, stirrer and drop funnel. 306 gram of acetic acid anhydride are added to the flask, whereupon 78.4 gram of anhydrous tin-(II)-fluoride is added.

A slurry is obtained to which are added, under strong agitation, 56.7 gram of hydrogen peroxide solution (30%). The addition of the solution takes place very slowly and in drop-wise manner. Because of the exothermic reaction, the reaction mixture heats up to about 90° C. The reaction time amounted to about 4 hours. Upon completion of the reaction, acetic acid is removed by distillation by way of a rotation evaporator in a water jet vacuum. The tin-diacetate-difluoride obtained in this manner is removed by filtration and is washed 5 times with 150 ml of chloroform each. Subsequently the product is dried in vacuum (about 2 mm Hg).

The yield was 220 gram of tin-diacetate-difluoride.

EXAMPLE 6

This experiment was carried out in a 250 ml four neck flask fitted with a distillation attachment, thermometer and stirrer. 61.5 gram of tin-diacetate-dichloride and 113.8 gram of stearic acid are added to the flask. This product mixture is heated under stirring to about 100° C. The acetic acid formed in this manner is removed by distillation, first in a water jet vacuum and subsequently in vacuum (about 2 mm Hg). The reaction period amounted to about 4 hours.

The yield was 148.8 gram of tin-dichloride-distearate.

EXAMPLE 7

This experiment was carried out in a 250 ml four neck flask fitted with a distillation attachment, thermometer and stirrer. 61.5 gram of tin-diacetate-dichloride and 110.2 gram of stearic acid anhydride are added to the flask. This product mixture is heated under stirring to about 100° C. The acetic acid anhydride formed during the procedure is removed by distillation, first in a water jet vacuum and subsequently in vacuum (about 2 mm Hg). The reaction time amounts to about 5 hours.

The yield was 151.2 gram of tin-dichloride-distearate.

EXAMPLE 8

This experiment was carried out in a 250 ml four neck flask fitted with a stirrer, distillation attachment and thermometer. 61.5 gram of tin-diacetate-dichloride and 46.5 gram of caproic acid are added to the flask. The mixture is heated under stirring to 110° C. Upon applying a slight vacuum, the acetic acid thus formed is removed by distillation and is received in a cooled receptacle. The reaction period amounts to about 2 hours.

The yield was 77.0 gram of tin-dichloride-dicapronate.

EXAMPLE 9

This experiment was carried out in a 250 ml four neck flask fitted with a stirrer, distillation attachment and thermometer. 61.9 gram of tin-tiacetate-dichloride and 58.8 gram of 2-ethyl-hexane acid are added to the flask. The mixture is heated under stirring and slight vacuum conditions to 110° C. The acetic acid formed in this manner is removed by distillation into a cooled receptable. The reaction period amounted to about 2.5 hours and the yield was 92.3 gram of tin-dichloride-di-2-ethyl-hexanoate.

EXAMPLE 10

This experiment was carried out in a 500 ml four neck flask fitted with a stirrer, distillation attachment and thermometer. 61.5 gram of tin-dichloride-diacetate and 80.1 gram of lauric acid are added. A slight vacuum is applied and the mixture is melted at about 45° C. and subsequently heated under stirring to 95° C. The acetic acid formed in this manner is received in a cooled receptacle. The reaction period amounted to about 2 hours and the yield was 119.6 gram of tin-dichloride-dilaurate.

EXAMPLE 11

This experiment was carried out in a 500 ml four neck flask fitted with a stirrer, distillation attachment and thermometer. 61.5 gram of tin-diacetate-dichloride and 136.2 gram of behen acid are added to the flask. The mixture is melted at about 80° C. and, upon application of a slight vacuum, is further heated to 120° C. The acetic acid formed in this manner is received in a cooled receptacle. The reaction period amounted to about 2 hours and the yield was 169.3 gram of tin-dichloride-dibehenate.

I claim:

1. A method of preparing anhydrous tin-diacetate-dihalide which comprises reacting anhydrous tin-(II)-halide with an excess amount of acetic acid anhydride at a temperature of about between 20° to 100° C. while passing oxygen through the reaction mixture or adding an oxygen yielding agent to the reaction mixture and separating the tin-diacetate-dihalide thus formed.

2. A method as claimed in claim 1, wherein said oxygen yielding agent is hydrogen peroxide.

3. A method for the preparation of anhydrous tin-dicarboxylate-dihalide which comprises:
   (a) preparing a reaction mixture of anhydrous tin-(II)-halide and an excess amount of acetic acid anhydride, passing oxygen or an oxygen yielding agent through the reaction mixture and heating the reaction mixture to a temperature of about between 20° to 100° C. to form tin-diacetate-dihalide;
   (b) separating the tin-diacetate-dihalide and reacting it with aliphatic carboxylic acid having more than four carbon atoms or its corresponding acid anhydride at a temperature of about between 80° and 150° C.; and
   (c) removing liberated acetic acid anhydride or acetic acid under vacuum conditions.

4. A method as claimed in claim 3, wherein step (b) is carried out with saturated or unsaturated aliphatic carboxylic acids with up to 22 carbon atoms or its corresponding acid anhydride.

5. A method as claimed in claim 3, wherein step (a) is carried out in the presence of acetic acid as solvent.

6. A method as claimed in claim 3, wherein said oxygen yielding agent is hydrogen peroxide solution, the water introduced into the reaction mixture by said solution being converted into acetic acid by the addition of acetic acid anhydride.

7. A method as claimed in claim 3, wherein step (a) is carried out at a temperature of about between 30° to 90° C. while step (b) is carried out at a temperature of about between 100° to 110° C.

* * * * *

UNITED STATES PATENT AND TRADEMARK OFFICE
CERTIFICATE OF CORRECTION

PATENT NO. : 5,068,374
DATED : November 26, 1991
INVENTOR(S) : Erich Ruf It is certified that error appears in the above-identified patent and that said Letters Patent is hereby corrected as shown below:

On the title page, Item [73] Assignee: Th. Goldschmidt AG, Essen, Fed. Rep. of Germany Signed and Sealed this Thirtieth Day of March, 1993

Attest:

STEPHEN G. KUNIN

*Attesting Officer*     Acting Commissioner of Patents and Trademarks